United States Patent [19]

Williams

[11] Patent Number: 5,443,794
[45] Date of Patent: Aug. 22, 1995

[54] MEASURING APPARATUS

[75] Inventor: Paul M. Williams, Barry, United Kingdom

[73] Assignee: Lion Technology Limited, Barry, United Kingdom

[21] Appl. No.: 698,198

[22] Filed: May 6, 1991

Related U.S. Application Data

[63] Continuation of Ser. No. 382,663, filed as PCT/GB88/00236, Mar. 29, 1988, abandoned.

[30] Foreign Application Priority Data

May 15, 1987 [GB] United Kingdom ............... 8711573

[51] Int. Cl.$^6$ ............................................. G01N 1/22
[52] U.S. Cl. ........................................ 422/84; 422/93; 436/132; 436/900; 73/23.3; 128/719
[58] Field of Search .................. 422/84, 93; 436/132, 436/900; 73/23.3; 128/719; 180/272

[56] References Cited

U.S. PATENT DOCUMENTS

| | | | |
|---|---|---|---|
| 3,830,630 | 8/1972 | Kiefer et al. | 422/84 |
| 4,132,109 | 1/1979 | VanderSyde | 73/23.3 |
| 4,278,636 | 7/1981 | Voigt et al. | 422/84 |
| 4,359,057 | 11/1982 | Manzella | 128/718 |
| 4,363,635 | 12/1982 | Hutson | 422/84 |
| 4,391,777 | 7/1983 | Hutson | 422/84 |
| 4,707,336 | 11/1987 | Jones | 422/84 |
| 4,749,553 | 6/1988 | Lopez et al. | 422/84 |

FOREIGN PATENT DOCUMENTS

| | | |
|---|---|---|
| 2577677 | 8/1986 | France . |
| WO83/04101 | 11/1983 | WIPO . |
| WO87/01204 | 2/1987 | WIPO . |

*Primary Examiner*—Lyle A. Alexander
*Attorney, Agent, or Firm*—Young & Thompson

[57] ABSTRACT

This invention relates to apparatus for measuring the concentration of a volatile component in a gas and in particular, but not exclusively, to breath alcohol testing apparatus.

In such apparatus 10, a pressure transducer 15 is provided to detect the ambient pressure during test. This pressure is used to modify the output of a fuel cell 11.

7 Claims, 1 Drawing Sheet

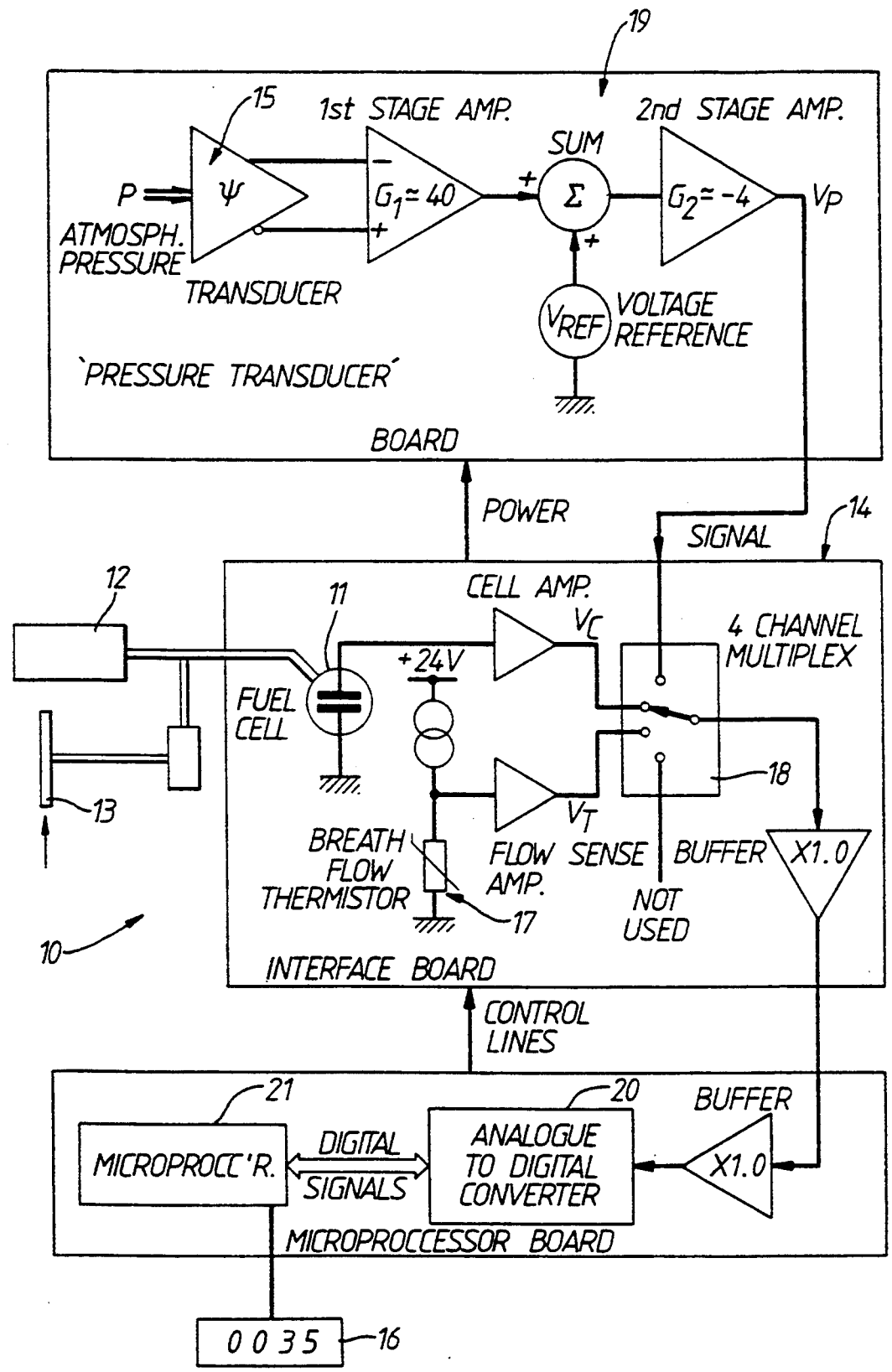

MEASURING APPARATUS

This application is a continuation of application Ser. No. 07/382,663, filed as PCT/GB88/00236, Mar. 29, 1988, now abandoned.

BACKGROUND OF THE INVENTION

1. Field of the Invention

This invention relates to apparatus for measuring the concentration of a volatile component in a gas and in particular, but not exclusively, to breath alcohol testing apparatus.

2. Description of the Prior Art

There are in general two types of breath alcohol testing apparatus; screening and evidential. For the latter the courts of most countries require that the detector for alcohol (ethanol) is re-calibrated before each breath sample is taken. One of the ways of achieving this calibration is to release into the detector a quantity of a gas containing a known concentration of ethanol from a pressurised cylinder which has been prepared in the laboratory. However, this concentration is only accurate for a single atmospheric pressure and accordingly the calibration can cause the detector to read too high or too low, depending on the altitude at which the reading is taken and the local ambient atmospheric conditions. To date attempts have been made to overcome this problem by artificially weighting the detector output in accordance with the altitude at which the reading is taken. This is unsatisfactory because the altitude is often not known accurately and the atmospheric pressure at any given altitude is not constant.

The present invention consists in apparatus for measuring the concentration of a volatile component in a gas, including a detector for detecting the volatile component and producing an output signal representing the concentration of the volatile component in the gas, a gas standard containing a predetermined concentration of the volatile component, sampling means for delivering either a test sample or a sample from the standard to the detector, means for measuring the atmospheric pressure and output means responsive to the pressure means and to the detector output signal for generating a representation of the measured concentration.

Preferably, the sampling means is arranged to deliver a standard sample to the detector prior to the delivery of each test sample.

The apparatus may have many uses, for example in the wine or chemical trades, but it is particularly suited for breath testing drivers and the like to see that they do not exceed legal limits of breath alcohol concentrations. In this case the test sample will not be subject to variation due to ambient pressure conditions and the output means may calculate the value of the measured concentration S from the following formula:

$$S = C \times \frac{Vc\ samp}{Vc\ cal} \times falt$$

wherein C is the concentration of volatile component in the gas standard

Vc samp is the value of the detector output signal for the test sample

Vc cal is the value of the detector output signal from the standard sample falt is the ratio of the measured pressure to a calibration pressure The pressure sensor may measure absolute pressure.

The detector may be a fuel cell, a semiconductor or an infrared detector or indeed any other suitable detector. It may operate in conjunction with a gas chromatographic column.

Although the invention has been defined above it is to be understood it includes any inventive combination of the features set out above or in the following description:

BRIEF DESCRIPTION OF THE DRAWINGS

The invention may be performed in various ways and a specific embodiment will now be described, by way of example, with reference to the accompanying drawing, which is a schematic circuit diagram of the circuitry of a breath testing apparatus.

DETAILED DISCUSSION

A breath testing apparatus is diagrammatically illustrated in the FIGURE and generally indicated at 10. The apparatus essentially comprises a fuel cell 11 which can be supplied with samples either from a gas standard in a pressurised cylinder 12 or a subject breath tube 13, processing circuitry 14, a pressure transducer 15 and a read-out 16.

The operation of the fuel cell is well known and will not be described in detail but it will be seen that it is provided with a breath flow detector at 17 to ensure that the sample is taken from the alveolar breath.

The outputs of the fuel cell 11 and the breath flow detector 17 are supplied to a multiplexer 18 which also receives a signal from the ambient pressure transducer 15 via suitable conditioning circuitry generally indicated at 19. The multiplexer 18 scans the various outputs and supplies them sequentially via an analogue to digital converter 20 to a microprocessor 21 which, having processed the signals set out below, provides a read-out at 16 corresponding to the concentrations of ethanol in the subject's breath.

The output of the transducer 15 as a function of the atmospheric pressure p is conditioned by the circuitry 19 to produce a voltage Vp in accordance with the following relationship:

$$Vp = \frac{p}{80.8} - 12.5$$

where p is measured in millibars. From this voltage the microprocessor can work out a pressure (altitude) correction factor falt where:

$$falt = \frac{p}{1010} = \frac{Vp}{12.5} + 1$$

This correction factor assumes that the gas standard has been prepared when the ambient pressure is at one atmosphere.

After the fuel cell has received samples both from the standard and from the subject's breath, the microprocessor applies the correction for atmospheric pressure because the concentration of the ethanol in the standard is proportional to it but the concentration of ethanol in the breath is (effectively) constant. Thus, a true breath ethanol concentration S can be calculated from the following formula:

$$S = C \times \frac{Vc\ samp}{Vc\ cal} \times falt$$

where C is the calibration concentration (i.e., the standards concentration at one atmosphere) and Vc samp and Vc cal are the respective fuel cell output voltages from the breath sample and the standard sample.

Thus, for a gas cylinder prepared at standard atmospheric pressure of 1010 mB the following examples will result:

| | | |
|---|---|---|
| p = 606 mB | Vp = 5.000 V | falt = 0.600 |
| | | (altitude = 4000 m) |
| p = 101 mB | Vp = 0.000 V | falt = 1,000 |
| p = 1100 mB | Vp = +1.114 V | falt = 1,089 |

It will be appreciated that the apparatus described above not only provides for variations in altitude, as are experienced in mountainous countries particularly when mobile units are being used, but also allows for local pressure variations. The result is a particularly accurate breath testing apparatus which will become more and more applicable as legal alcohol level limits drop and errors become more and more significant.

I claim:

1. Apparatus for measuring the concentration of a volatile component in a gas, including a detector for detecting the volatile component and producing an output signal representing the detected concentration of the volatile component in the gas, a gas standard containing a predetermined concentration of the volatile component in a diluent gas pressurized in a container, the standard being prepared for a predetermined atmospheric pressure, sampling means for delivering alternately a sample from the standard and a test sample to the detector, means for outputting from the detector successively one signal representative of the concentration of the volatile component in the test sample and another signal representative of the concentration of the volatile component in the sample from the standard, means for measuring the ambient atmospheric pressure when the sample from the standard is delivered, means for determining the difference between the measured ambient atmospheric pressure and said predetermined atmospheric pressure, means for generating a correction signal in accordance with said difference, means for generating a concentration signal from said one and said another signals, and means for correcting the concentration signal in accordance with the correction signal and for displaying the result as an indication of the concentration of the volatile component in a source from which said test sample was taken.

2. Apparatus as claimed in claim 1, wherein the sampling means is arranged to deliver a standard sample to the detector prior to the delivery of each test sample.

3. Apparatus as claimed in claim 1, wherein the apparatus constitutes breath testing apparatus.

4. Apparatus as claimed in claim 1 wherein the output means includes calculating means for calculating the value of the measured concentration S from the following formula:

$$S = C \times \frac{Vc\ samp}{Vc\ cal} \times falt$$

wherein C is the concentration of volatile component in the standard sample

Vc samp is the value of the detector output signal for the test sample

Vc cal is the value of the detector output signal from the standard sample; and falt is the ratio of the measured ambient atmospheric pressure to said predetermined atmospheric pressure.

5. Apparatus as claimed in claim 1, wherein the pressure sensor measures absolute pressure.

6. Apparatus as claimed in claim 1, wherein the detector is a fuel cell, a semiconductor or an infrared detector.

7. Apparatus for measuring the concentration of a volatile component in a gas, including a detector for detecting the volatile component and producing an output signal representing the detected concentration of the volatile component in the gas, a gas standard containing a predetermined concentration of the volatile component in a diluent gas pressurized in a container, the standard being prepared for a predetermined atmospheric pressure, sampling means for delivering alternately a sample from the standard and a test sample to the detector, means for outputting from the detector successively one signal representative of the concentration of the volatile component in the test sample and another signal representative of the concentration of the volatile component in the sample from the standard, means for measuring the ambient atmospheric pressure when the sample from the standard is delivered, means for determining the difference between the measured ambient atmospheric pressure and said predetermined atmospheric pressure, means for generating a correction signal in accordance with said difference, and means for correcting said another signal in accordance with the correction signal, said apparatus further comprising display means for displaying a value indicative of a corrected volatile gas concentration.

* * * * *